(12) United States Patent
Resconi et al.

(10) Patent No.: US 8,003,743 B2
(45) Date of Patent: Aug. 23, 2011

(54) METALLOCENE COMPOUNDS, LIGANDS USED IN THEIR PREPARATION, PREPARATION OF 1-BUTENE POLYMERS AND 1-BUTENE POLYMERS THEREFROM

(75) Inventors: Luigi Resconi, Ferrara (IT); Friederike Morhard, Bangkok (TH)

(73) Assignee: Basell Poliolefine Italia, S.R.L., Milan (IT)

( * ) Notice: Subject to any disclaimer, the term of this patent is extended or adjusted under 35 U.S.C. 154(b) by 815 days.

(21) Appl. No.: 11/632,383

(22) PCT Filed: May 31, 2005

(86) PCT No.: PCT/EP2005/052486
§ 371 (c)(1),
(2), (4) Date: Jan. 12, 2007

(87) PCT Pub. No.: WO2006/005648
PCT Pub. Date: Jan. 19, 2006

(65) Prior Publication Data
US 2008/0139762 A1  Jun. 12, 2008

Related U.S. Application Data

(60) Provisional application No. 60/590,660, filed on Jul. 23, 2004.

(30) Foreign Application Priority Data

Jul. 13, 2004 (EP) ..................................... 04103351

(51) Int. Cl.
C08F 10/00 (2006.01)
C08F 10/08 (2006.01)
C08F 110/00 (2006.01)
C08F 110/08 (2006.01)
C08F 210/00 (2006.01)
C08F 210/08 (2006.01)
C08F 210/16 (2006.01)

(52) U.S. Cl. ...................... 526/348.6; 526/170; 526/172; 526/183; 526/192; 526/194; 526/222; 526/348; 502/152; 502/155; 502/158; 502/168; 502/219; 502/227; 502/232

(58) Field of Classification Search .................. 526/170, 526/172, 183, 192, 194, 222, 348.6
See application file for complete search history.

(56) References Cited

U.S. PATENT DOCUMENTS

| H179 H | * | 12/1986 | Klingensmith et al. ... 526/124.9 |
| 6,482,902 B1 | | 11/2002 | Bohnen et al. |
| 6,953,829 B2 | | 10/2005 | Kratzer et al. |
| 7,101,940 B2 | | 9/2006 | Schottek et al. |

FOREIGN PATENT DOCUMENTS

| DE | 19962814 | 6/2001 |
| DE | 19962910 | 7/2001 |
| EP | 172961 | 3/1986 |
| EP | 1260525 | 11/2002 |
| WO | 91/02012 | 2/1991 |
| WO | 92/00333 | 1/1992 |
| WO | 99/21899 | 5/1999 |
| WO | 99/24446 | 5/1999 |

(Continued)

OTHER PUBLICATIONS

L. Resconi et al., "1-Olefin Polymerization at Bis(pentamethylcyclopentadienyl)zirconium and -hafnium Centers: Enantioface Selectivity," *Macromolecules*, vol. 25(25), p. 6814-6817 (1992).

Primary Examiner — Vasu Jagannathan
Assistant Examiner — Richard A Huhn
(74) Attorney, Agent, or Firm — Dilworth IP, LLC

(57) ABSTRACT

A process for preparing 1-butene polymers comprising polymerizing 1-butene and optionally ethylene, propylene or higher alpha-olefin, in the presence of a catalyst system obtainable by contacting:
a) metallocene compound of formula (I):

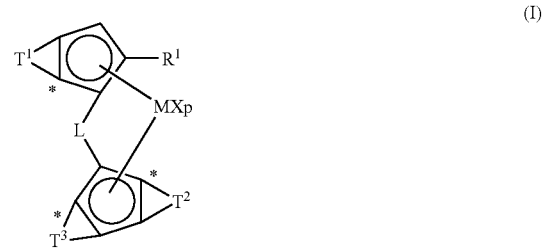

wherein: M is a transition metal; p is an integer from 0 to 3; X, same or different, is a hydrogen atom, a halogen atom, or a hydrocarbon group; L is a divalent $C_1$-$C_{40}$ hydrocarbon radical; $R^1$ is a $C_1$-$C_{40}$ hydrocarbon radical; $T^1$, is a moiety of formula (IIa) or (IIb):

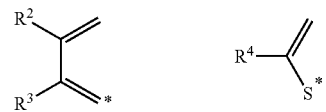

wherein $R^2$ and $R^3$, are $C_1$-$C_{40}$ hydrocarbon radicals or they can form together a $C_3$-$C_7$-membered ring; $R^4$ is $C_1$-$C_{40}$ hydrocarbon radicals; $T^2$ and $T^3$, are a moiety of formula (IIIa) or (IIIb):

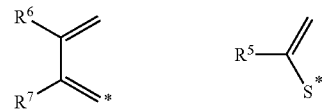

wherein $R^6$ and $R^7$, equal to or different from each other, are hydrogen atoms or $C_1$-$C_{40}$ hydrocarbon radicals; $R^5$ is a hydrogen atom or a $C_1$-$C_{40}$ hydrocarbon radicals; with the proviso that if $T^1$ is a moiety of formula (IIa) at least one between $T^2$ and $T^3$ is a moiety of formula (IIIb), and if $T^1$ is a moiety of formula (IIb) at least one between $T^2$ and $T^3$ is a moiety of formula (IIIa); and
b) at least an alumoxane or a compound able to form an alkylmetallocene cation.

16 Claims, No Drawings

FOREIGN PATENT DOCUMENTS

| | | |
|---|---|---|
| WO | 99/40129 | 8/1999 |
| WO | 99/45043 | 9/1999 |
| WO | 01/21674 | 3/2001 |
| WO | 01/44318 | 6/2001 |
| WO | 01/47939 | 7/2001 |
| WO | 01/48039 | 7/2001 |
| WO | 01/48040 | 7/2001 |
| WO | 01/62764 | 8/2001 |
| WO | 01/70878 | 9/2001 |
| WO | 02/100908 | 12/2002 |
| WO | 02/100909 | 12/2002 |
| WO | 03/000706 | 1/2003 |
| WO | 03/014107 | 2/2003 |
| WO | 03/042258 | 5/2003 |
| WO | WO 03/042258 * | 5/2003 |
| WO | 03/070778 | 8/2003 |
| WO | 03/099883 | 12/2003 |
| WO | 2004/099269 | 11/2004 |

* cited by examiner

METALLOCENE COMPOUNDS, LIGANDS USED IN THEIR PREPARATION, PREPARATION OF 1-BUTENE POLYMERS AND 1-BUTENE POLYMERS THEREFROM

The present invention relates to a process for polymerizing 1-butene by using a bridged metallocene compound wherein one n-ligand is a substituted-indenyl. The present invention further relates to the 1-butene polymers obtained by said process and to the metallocene compounds able to produce said 1-butene polymers.

1-Butene polymers are well known in the art. In view of their good properties in terms of pressure resistance, creep resistance, and impact strength, they are widely used for example in the manufacture of pipes for metal pipe replacement, easy-open packaging and films.

The 1-butene (co)polymers are generally prepared by polymerizing 1-butene in the presence of $TiCl_3$ based catalyst components together with diethylaluminum chloride (DEAC) as cocatalyst. In some cases mixtures of diethyl aluminum iodide (DEAI) and DEAC are used. The polymers obtained, however, generally do not show satisfactory mechanical properties. Furthermore, in view of the low yields obtainable with the $TiCl_3$ based catalysts, the 1-butene polymers prepared with these catalysts have a high content of catalyst residues (generally more than 300 ppm of Ti) which lowers the properties of the polymers and makes necessary to carry out a subsequent deashing step.

1-Butene (co)polymers can also be obtained by polymerizing the monomers in the presence of a stereospecific catalyst comprising: (A) a solid component comprising a Ti compound and an electron-donor compound supported on $MgCl_2$; (B) an alkylaluminum compound and, optionally, (C) an external electron-donor compound. A process of this type is disclosed in EP-A-172961 and WO99/45043.

Recently metallocene compounds have been used for producing 1-butene polymers. For example WO 02/100908, WO 02/100909, WO 03/014107 disclose several classes of metallocene-based catalyst system able to give in high yield 1-butene polymers having a quite high level of isotacticity.

In all these documents the 1-butene polymers described are endowed with quite high melting points and isotacticity (mmmm pentads).

1-butene polymer having low isotacticity and low elastic modulus can substitute flexible polyvinyl chloride-based resins or it can be used as blend component for improving the flexibility of the resulting resin. Low modulus 1-butene polymers are described in EP 1 260 525, said polymers are obtained by using a double bridged metallocene compound that is completely different from the metallocene compound used in the process of the present invention. Moreover the 1-butene polymers obtained with the process of the present invention show an improved balance between elastic modulus and melting point, with respect to the polymers obtained in EP 1 260 525.

Thus the problem that the present invention wants to solve is to find process able to give 1-butene polymers having a low elastic modulus, a high molecular weight in high yield.

An object of the present invention is a process for preparing 1-butene polymers optionally containing up to 30% by mol of units derived from at least one monomer selected from ethylene, propylene or an alpha olefin of formula $CH_2=CHZ'$, wherein $Z'$ is a $C_3-C_{10}$ alkyl group, comprising polymerizing 1-butene and optionally ethylene, propylene or said alpha-olefin, in the presence of a catalyst system obtainable by contacting:

a) at least a metallocene compound of formula (I):

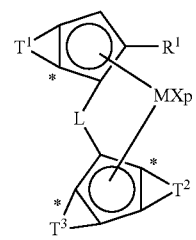

(I)

wherein:

M is a transition metal belonging to group 3, 4, 5, 6 or to the lanthanide or actinide groups in the Periodic Table of the Elements; preferably M is titanium, zirconium or hafnium;

p is an integer from 0 to 3, preferably p is 2, being equal to the formal oxidation state of the metal M minus 2;

X, same or different, is a hydrogen atom, a halogen atom, or a R, OR, $OSO_2CF_3$, OCOR, SR, $NR_2$ or $PR_2$ group, wherein R is a are linear or branched, cyclic or acyclic, $C_1-C_{40}$-alkyl, $C_2-C_{40}$ alkenyl, $C_2-C_{40}$ alkynyl, $C_6-C_{40}$-aryl, $C_7-C_{40}$-alkylaryl or $C_7-C_{40}$-arylalkyl radicals; optionally containing heteroatoms belonging to groups 13-17 of the Periodic Table of the Elements; preferably R is a linear or branched $C_1-C_{20}$-alkyl radical; or two X can optionally form a substituted or unsubstituted butadienyl radical or a OR'O group wherein R' is a divalent radical selected from $C_1-C_{40}$ alkylidene, $C_6-C_{40}$ arylidene, $C_7-C_{40}$ alkylarylidene and $C_7-C_{40}$ arylalkylidene radicals; preferably X is a hydrogen atom, a halogen atom or a R group; more preferably X is chlorine or a $C_1-C_{10}$-alkyl radical; such as methyl, or ethyl radicals;

L is a divalent $C_1-C_{40}$ hydrocarbon radical optionally containing heteroatoms belonging to groups 13-17 of the Periodic Table of the Elements or a divalent silylidene radical containing up to 5 silicon atom; preferably L is a divalent bridging group selected from $C_1-C_{40}$ alkylidene, $C_3-C_{40}$ cycloalkylidene, $C_6-C_{40}$ arylidene, $C_7-C_{40}$ alkylarylidene, or $C_7-C_{40}$ arylalkylidene radicals optionally containing heteroatoms belonging to groups 13-17 of the Periodic Table of the Elements, and silyliene radical containing up to 5 silicon atoms such as $SiMe_2$, $SiPh_2$; preferably L is a group $(Z(R'')_2)_n$ wherein Z is a carbon or a silicon atom, n is 1 or 2 and R'' is a $C_1-C_{20}$ hydrocarbon radical optionally containing heteroatoms belonging to groups 13-17 of the Periodic Table of the Elements; preferably R'' is a linear or branched, cyclic or acyclic, $C_1-C_{20}$-alkyl, $C_2-C_{20}$ alkenyl, $C_2-C_{20}$ alkynyl, $C_6-C_{20}$-aryl, $C_7-C_{20}$-alkylaryl or $C_7-C_{20}$-arylalkyl radicals optionally containing heteroatoms belonging to groups 13-17 of the Periodic Table of the Elements; more preferably the group $(Z(R'')_2)_n$ is $Si(CH_3)_2$, $SiPh_2$, $SiPhMe$, $SiMe(SiMe_3)$, $CH_2$, $(CH_2)_2$, and $C(CH_3)_2$; even more preferably $(Z(R'')_2)_n$ is $Si(CH_3)_2$.

$R^1$ is a $C_1-C_{40}$ hydrocarbon radical optionally containing heteroatoms belonging to groups 13-17 of the Periodic Table of the Elements; preferably $R^1$ is a linear or branched, cyclic or acyclic, $C_1-C_{40}$-alkyl, $C_2-C_{40}$ alkenyl, $C_2-C_{40}$ alkynyl, $C_6-C_{40}$-aryl, $C_7-C_{40}$-alkylaryl or $C_7-C_{40}$-arylalkyl radical; optionally containing heteroatoms belonging to groups 13-17 of the Periodic Table of the Elements; more preferably $R^1$ is a linear or branched, saturated or unsaturated $C_1-C_{20}$-alkyl radical; more preferably $R^1$ is a methyl or ethyl radical;

$T^1$ is a moiety of formula (IIa) or (IIb);:

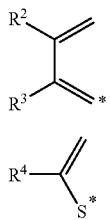

(IIa)

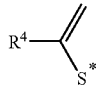

(IIb)

wherein the atom marked with the symbol * bonds the atom marked with the same symbol in the compound of formula (I);

$R^2$ and $R^3$, equal to or different from each other, are $C_1$-$C_{40}$ hydrocarbon radicals optionally containing heteroatoms belonging to groups 13-17 of the Periodic Table of the Elements or they can form together a condensed saturated or unsaturaded $C_3$-$C_7$-membered ring, preferably a $C_4$-$C_6$-membered ring, optionally containing heteroatoms belonging to groups 13-16 of the Periodic Table of the Elements; every atom forming said ring being substituted with $R^8$ radicals; that means that the valence of each atom forming said ring is filled with $R^8$ groups, wherein $R^8$, equal to or different from each other, are hydrogen atoms or $C_1$-$C_{40}$ hydrocarbon radicals; preferably $R^8$ are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing one or more heteroatoms belonging to groups 13-17 of the Periodic Table of the Elements; more preferably $R^8$ are a hydrogen atoms or a linear or branched, saturated or unsaturated $C_1$-$C_{20}$-alkyl radicals; even more preferably $R^8$ are a hydrogen atoms or a methyl or ethyl radicals;

$R^4$ is $C_1$-$C_{40}$ hydrocarbon radical optionally containing heteroatoms belonging to groups 13-17 of the Periodic Table of the Elements; preferably $R^4$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical optionally containing one or more heteroatoms belonging to groups 13-17 of the Periodic Table of the Elements; more preferably $R^4$ is a linear or branched, cyclic or acyclic, $C_1$-$C_{40}$-alkyl $C_6$-$C_{40}$-aryl, $C_7$-$C_{40}$-arylalkyl radical such as a methyl, ethyl, phenyl or phenyl radical said phenyl radical being optionally substituted with one or more $C_1$-$C_{10}$ alkyl radicals;

preferably the moiety $T^1$ has formula (IIa);

$T^2$ and $T^3$, equal to or different from each other, are a moiety of formula (IIIa) or (IIIb):

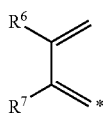

(IIIa)

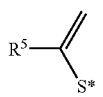

(IIIb)

wherein the atom marked with the symbol * bonds the atom marked with the same symbol in the compound of formula (I);

$R^6$ and $R^7$, equal to or different from each other, are hydrogen or $C_1$-$C_{40}$ hydrocarbon radicals optionally containing heteroatoms belonging to groups 13-17 of the Periodic Table of the Elements; preferably $R^6$ and $R^7$, equal to or different from each other, are hydrogen atoms or linear or branched, cyclic or acyclic, $C_1$-$C_{40}$-alkyl, $C_2$-$C40$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing one or more heteroatoms belonging to groups 13-17 of the Periodic Table of the Elements; more preferably $R^6$ and $R^7$ are hydrogen atoms;

$R^5$ is a hydrogen atom or a $C_1$-$C_{40}$ hydrocarbon radical optionally containing heteroatoms belonging to groups 13-17 of the Periodic Table of the Elements; preferably $R^5$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical optionally containing one or more heteroatoms belonging to groups 13-17 of the Periodic Table of the Elements; even more preferably $R^5$ is a hydrogen atom or a linear or branched, cyclic or acyclic, $C_1$-$C_{40}$-alkyl $C_6$-$C_{40}$-aryl, $C_7$-$C_{40}$-arylalkyl radical such as a methyl, ethyl, phenyl or phenyl radical said phenyl radical being optionally substituted with one or more $C_1$-$C_{10}$ alkyl radicals;

preferably $T^2$ and $T^3$ are the same; more preferably $T^2$ and $T^3$ are moiety of formula (IIIb);

with the proviso that if $T^1$ is a moiety of formula (IIa) at least one between $T^2$ and $T^3$ is a moiety of formula (IIIb), and if $T^1$ is a moiety of formula (IIb) at least one between $T^2$ and $T^3$ is a moiety of formula (IIIa);

b) at least an alumoxane or a compound able to form an alkylmetallocene cation; and c) optionally an organo aluminum compound.

Preferably the compound of formula (I) has formulas (IVa), (IVb), (IVc), or (IVd):

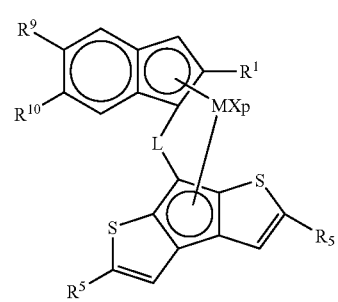

(VIa)

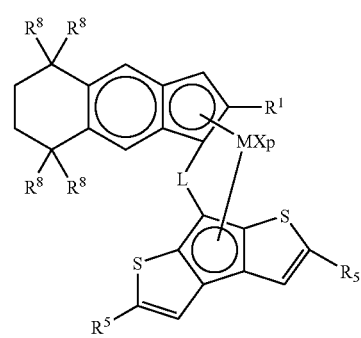

(IVb)

-continued

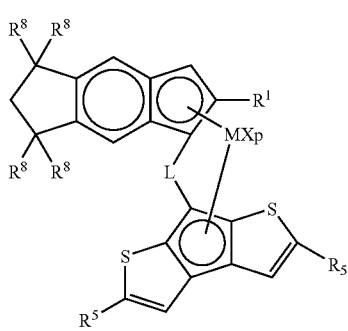

(IVc)

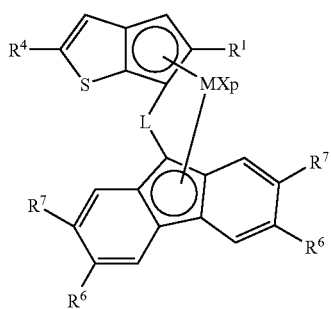

(IVd)

wherein

M, X, p, L, $R^1$, $R^4$ $R^5$, $R^6$, and $R^7$ have the meaning described above; $R^9$ and $R^{10}$, equal to or different from each other, are linear or branched, cyclic or acyclic, $C_1$-$C_{40}$-alkyl radicals;

preferably $R^9$ and $R^{10}$ are $C_1$-$C_{20}$-alkyl radicals, such as methyl, ethyl and isopropyl radicals;

$R^8$ are hydrogen atoms or linear or branched, saturated or unsaturated $C_1$-$C_{20}$-alkyl radical;

more preferably $R^8$ are hydrogen atoms or methyl radicals.

A further object of the present invention are metallocene compounds of formula (I) as described above; preferably the compound of formula (I) have formulas (IVa), (IVb), (IVc), or (IVd).

A further object of the present invention is a ligand of formula (V)

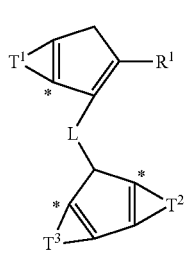

(V)

and/or its double bond isomers wherein $R^1$, $T^1$, $T^2$, $T^3$ and L have the meaning described above.

Compounds of formula (I) can be prepared with a process comprising the following steps:

a) contacting a ligand of formula (V)

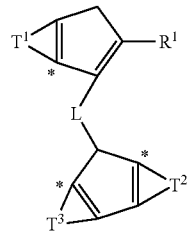

(V)

and/or its double bond isomers wherein $R^1$, $T^1$, $T^2$, $T^3$ and L have the meaning described above with a base selected from $T^a_jB$, $T^aMgT^b$, sodium and potassium hydride, metallic sodium and potassium, wherein B is an alkaline or alkali-earth metal; and j is 1 or 2, j being equal to 1 when B is an alkaline metal, preferably lithium, and j being equal to 2 when B is an alkali-earth metal; $T^a$ is a linear or branched, saturated or unsaturated $C_1$-$C_{20}$ alkyl, $C_3$-$C_{20}$ cycloalkyl, $C_6$-$C_{20}$ aryl, $C_7$-$C_{20}$ alkylaryl or $C_7$-$C_{20}$ arylalkyl group, optionally containing one or more Si or Ge atoms; preferably $T^a$ is methyl or butyl radical; $T^b$ is an halogen atom or a group OR''' wherein R''' is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing one or more heteroatoms belonging to groups 13-17 of the Periodic Table of the Elements; preferably $T^b$ is an halogen atom, more preferably bromine; wherein the molar ratio between said base and the ligand of the formula (V) and is at least 2:1; excess of said base can be used; and b) contacting the product obtained in step a) with a compound of formula $MX_{p+2}$ wherein M and X have the meaning described above.

The process is preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from $-100°$ C. to $+80°$ C., more preferably from $-20°$ C. to $+70°$ C.

The ligands of formula (V) can be obtained with a process comprising the following steps:

a) contacting a compound of formula (VIa):

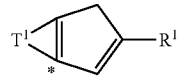

(VIa)

and/or its double bond isomer wherein $T^1$, and $R^1$ are defined as above;

with a base selected from $T^a_jB$, $T^aMgT^b$, sodium and potassium hydride, metallic sodium and potassium; wherein $T^a$, j, B and $T^b$ are defined as above, and wherein the molar ratio between said base and the compound of the formula (VIa) is at least 1:1; excess of said base can be used;

b) contacting the anionic compound obtained in step a) with a compound of formula (VIb):

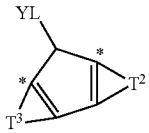
(VIb)

wherein T², T³ and L are defined as above and Y is chlorine, bromine and iodine, preferably Y is chlorine or bromine.

In an alternative embodiment the process for preparing the ligand of formula (V) comprises the following steps:

a) contacting a compound of formula (VIc):

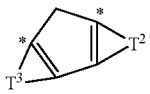
(VIc)

wherein T², T³ are defined as above; with a base selected from $T^a{}_jB$, $T^aMgT^b$, sodium and potassium hydride, metallic sodium and potassium; wherein $T^a$, j, B, and $T^b$ are defined as above, and wherein the molar ratio between said base and the compound of the formula (VIc) is at least 1:1, excess of said base can be used;

b) contacting the anionic compound obtained in step a) with a compound of formula (VId):

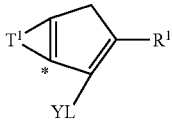
(VId)

wherein R¹, T¹ and L are defined as above; and Y is chlorine, bromine and iodine, preferably Y is chlorine or bromine.

Compounds of formula (IVa), (IVb), (IVc), or (IVd) can be obtained by the processes described above starting from the ligands of formula (Va), (Vb), (Vc) or (Vd):

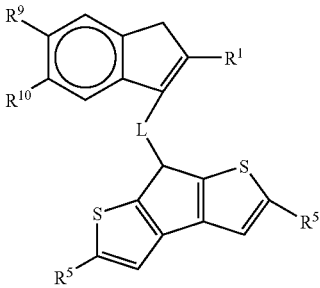
(Va)

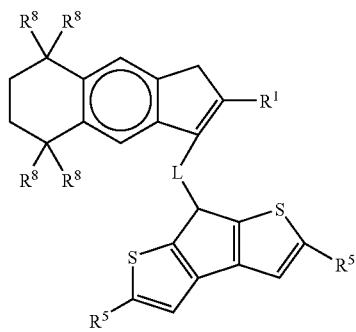
(Vb)

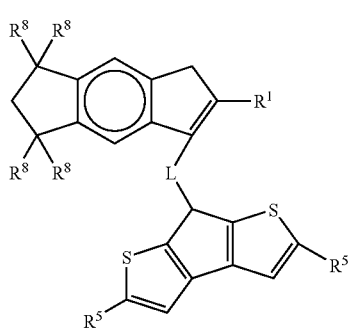
(Vc)

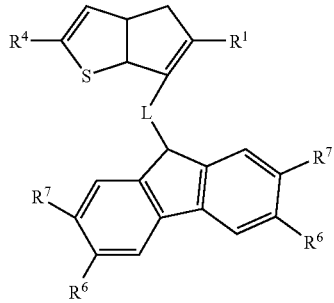
(Vd)

or their double bonds isomers
wherein R¹, R⁴, R⁵, R⁶, R⁷, R⁸, R⁹, R¹⁰ and L have the meaning described above.

The ligands of formula (Va), (Vb), (Vc) or (Vd) can be prepared according to the process described above starting from the appropriate compounds.

Alumoxanes used as component b) in the catalyst system according to the present invention can be obtained by reacting water with an organo-aluminium compound of formula $H_jAlU_{3-j}$ or $H_jAl_2U_{6-j}$, where the U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or $C_7$-$C_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The alumoxanes used in the process according to the invention are considered to be linear, branched or cyclic compounds containing at least one group of the type:

wherein the substituents U, same or different, are defined above.

In particular, alumoxanes of the formula:

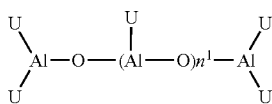

can be used in the case of linear compounds, wherein $n^1$ is 0 or an integer of from 1 to 40 and the substituents U are defined as above; or alumoxanes of the formula:

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl) aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl) aluminium, tris(2-ethyl-3-methyl-butyl)aluminium, tris(2-ethyl-3-methyl-pentyl)aluminium, tris(2,3-diethyl-pentyl) aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl) aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluorophenyl)-propyl]aluminium, tris[2-(4-chloro-phenyl)-propyl] aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl] aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl) aluminium (TDMBA) and tris(2,3,3-trimethylbutyl) aluminium (TTMBA) are preferred.

Non-limiting examples of compounds able to form an alkylmetallocene cation are compounds of formula $D^+E^-$, wherein $D^+$ is a Brnsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer.

Preferably, the anion $E^-$ comprises one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakispentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylbenzylammonium-tetrakispentafluorophenylborate,
N,N-Dimethylhexylamonium-tetrakispentafluorophenylborate,
N,N-Dimethylaniliniumtetra(phenyl)borate,
N,N-Diethylaniliniumtetra(phenyl)borate,
N,N-Dimethylaniliniumtetrakis(pentafluorophenyl)borate,
N,N-Dimethylaniliniumtetrakis(pentafluorophenyl)aluminate,
N,N-Dimethylbenzylammonium-tetrakispentafluorophenylborate,
N,N-Dimethylhexylamonium-tetrakispentafluorophenylborate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate, and
N,N-Dimethylaniliniumtetrakis(pentafluorophenyl)borate.

Organic aluminum compounds used as compound c) are those of formula $H_jAlU_{3-j}$ or $H_jAl_2U_{6-j}$ as described above.

The polymerization process of the present invention can be carried out in liquid phase, optionally in the presence of an inert hydrocarbon solvent. Said hydrocarbon solvent can be either aromatic (such as toluene) or aliphatic (such as propane, hexane, heptane, isobutane, cyclohexane and 2,2,4-trimethylpentane). Preferably, the polymerization process of the present invention is carried out by using liquid 1-butene as polymerization medium.

The polymerization temperature preferably ranges from 0° C. to 250° C.; preferably comprised between 20° C. and 150° C. and, more particularly between 50° C. and 90° C.;

The molecular weight distribution can be varied by using mixtures of different metallocene compounds or by carrying out the polymerization in several stages which differ as to the polymerization temperature and/or the concentrations of the molecular weight regulators and/or the monomers concentration. Moreover by carrying out the polymerization process by using a combination of two different metallocene compounds of formula (I) a polymer endowed with a broad melting is produced.

According to the present invention 1-butene can be homopolymerized or copolymerized with ethylene, propylene or alpha olefins of formula $CH_2=CHZ'$ wherein $Z'$ is a $C_3$-$C_{10}$ alkyl group. When 1-butene is copolymerized with said comonomers, a copolymer having a content of comonomer derived units of up to 30% by mol can be obtained, preferably up to 20% by mol, more preferably from 0.2% by mol to 10% by mol. Examples of alpha-olefins of formula $CH_2=CHZ'$ are 1-pentene, 4-methyl-1-pentene, 1-hexene, 1-octene, 4,6-dimethyl-1-heptene, 1-decene, 1-dodecene. Preferred comonomers to be used in the process according to the present invention are ethylene, propylene and 1-hexene. Preferably with the process of the present invention 1-butene is homopolymerized.

When 1-butene is used according of the process of the present invention to obtain 1-butene homopolymer, the latter is endowed with a very low elastic modulus, with respect to the melting point. Moreover the isotacticity of the 1-butene homopolymer expressed as the percentage of the isotactic mmmm pentads measured with a $^{13}$C-NMR spectra according to the procedure described in the examples is comprised between 40% and 85%. While the melting point, measured according to the procedure described in the example, of the 1-butene homopolymer is comprised between 40° C. and 85° C. With these features said homopolymer has an optimum balance of elastomeric properties.

Therefore a further object of the present invention is a 1-butene homopolymer, that can be obtained according to the process of the present invention, having the following characteristics:

flexural modulus (FM) (ISO 527-1) comprised between 50 and 200 MPa; preferably between 50 and 150 MPa;
melting point (Tm) comprised between 40° C. and 80° C.; preferably between 45° C. and 75° C.; more preferably between 50° C. and 72° C.;
the flexural modulus (FM) (Mpa) and the melting point (Tm) (° C.) meet the following relation:

$FM<0.006Tm^{2.44}$ preferably the relation is $FM<0.005Tm^{2.44}$ intrinsic viscosity (I.V.) measured in tetrahydronaphtalene (THN) at 135° C.>0.5 dl/g, preferably ≧0.8 dl/g, more preferably >1 dl/g; even more preferably >1.2 dl/g; and isotactic pentads (mmmm) comprised between 40% and 80%, preferably comprised between 50% and 75%;

Preferably the 1-butene homopolymer has a molecular weight distribution Mw/Mn<4, preferably <3.5; more preferably <3.

The 1-butene polymers, especially 1-butene homopolymers obtained according to the process of the present invention can be suitable as component in a blend containing as further component a 1-butene-based polymer having high elastic modulus and high melting point. In this way it is possible to combine the best features of the two products that are completely miscible and thus obtaining a 1-butene-based polymer composition having high melting point and low elastic modulus. Therefore a further object of the present invention is a 1-butene polymer composition comprising:

A) from 10 to 90% by weigh of a 1-butene homopolymer or a 1-butene copolymer containing up to 30% by mol, preferably up to 20% by mol, more preferably from 0.2% by mol to 10% by mol of derived units of ethylene, propylene or alpha-olefins of formula $CH_2=CHZ'$ wherein $Z'$ is a $C_3$-$C_{10}$ alkyl group having the following characteristics:

flexural modulus (FM) (ISO 178) comprised between 50 and 200 MPa; preferably between 50 and 150 MPa;
melting point (Tm) comprised between 40° C. and 80° C.; preferably between 45° C. and 75° C.; more preferably between 50° C. and 72° C.;
the flexural modulus (FM) (Mpa) and the melting point (Tm) (° C.) meet the following relation:

$FM<0.006Tm^{2.44}$ preferably the relation is $FM<0.005Tm^{2.44}$ intrinsic viscosity (I.V.) measured in tetrahydronaphtalene (THN) at 135° C.>0.5 dl/g, preferably ≧0.8 dl/g, more preferably >1 dl/g; even more preferably >1.2 dl/g; and B) from 10 to 90% by weight of a 1-butene polymer selected from isotactic homopolymer of 1-butene, isotactic copolymer of 1-butene containing up to 2% by mol of ethylene derived units, isotactic copolymer of 1-butene containing up to 30% by mol of propylene derived units or an isotactic copolymer of 1-butene and one or more alpha olefins of formula $CH_2=CHZ'$, wherein $Z'$ is a $C_3$-$C_{10}$ alkyl group, containing up to 20% by mol of derived units of said alpha-olefins; said 1-butene polymer having the following characteristics:

melting point (Tm) higher than 90° C.; preferably higher than 100° C.; and
isotactic pentads (mmmm) higher than 90% preferably higher than 94%.

Preferably the 1-butene polymer A) has a molecular weight distribution Mw/Mn<4, preferably <3.5; more preferably <3. Preferably the 1-butene polymer B) has a molecular weight distribution Mw/Mn<4, preferably <3.5; more preferably <3. Preferably the 1-butene polymer A) the isotactic pentads (mmmm) are comprised between 40% and 80%, preferably comprised between 50% and 75%; Preferably the 1-butene polymer A) is a 1-butene homopolymer.

The 1-butene polymer B) can be obtained either by using titanium-based catalyst system supported on $MgCl_2$ or by using single-site based catalyst system such as for example metallocene-based catalyst system. Useful processes for obtaining this kind of polymers is described for example in WO 99/45043; WO 03/099883 EP 172961, WO 02/100908, WO 02/100909 WO 03/014107 and EP03101304.8.

When component B) of the composition according to the present invention is obtained by using a single-site based catalyst system; preferably a metallocene-based catalyst system, it is endowed with a molecular weight distribution (Mw/Mn) equal to or lower than 5; preferably lower than 4; more preferably lower than 3.

When component B) is obtained by using titanium-based catalyst system supported on $MgCl_2$, it is endowed with a molecular weight distribution higher than 3; preferably higher than 4; more preferably higher than 5.

Preferably the 1-butene polymer B) is a 1-butene homopolymer.

Preferably in the 1-butene polymer composition, object of the present invention, component A) ranges from 20 to 80% by weight; more preferably from 30 to 70% by weight; even more preferably from 40 to 60% by weight: component B) ranges from 20 to 80% by weight; more preferably from 30 to 70% by weight; even more preferably from 40 to 60% by weight.

The following compositions are also possible:

| component A | component B |
|---|---|
| 10-20% by weight | 90-80% by weight |
| 20-30% by weight | 80-70% by weight |
| 30-40% by weight | 70-60% by weight |
| 40-50% by weight | 60-50% by weight |
| 50-60% by weight | 50-40% by weight |
| 60-70% by weight | 40-30% by weight |
| 70-80% by weight | 30-20% by weight |
| 80-90% by weight | 20-10% by weight |

The metallocene compounds of formulas (I), (Va), (Vb), (Vc) or (Vd) can be also used for (co)polymerizing alpha-olefins, of formula $CH_2=CHZ''$ wherein $Z''$ is hydrogen or a $C_1$-$C_{20}$ alkyl group. Therefore a further object of the present invention is a process for (co)polymerizing alpha-olefins of formula $CH_2=CHZ''$ comprising contacting under polymerization conditions one or more of said alpha-olefins of formula $CH_2=CHZ''$ in the presence of a catalyst system obtainable by contacting:

a) a metallocene compound of formula (I);

b) at least an alumoxane or a compound able to form an alkylmetallocene cation; and c) optionally an organo aluminum compound.

Preferably the metallocene compound has formula (Va), (Vb), (Vc) or (Vd).

Examples of alpha olefins of formula $CH_2=CHZ''$ are ethylene, propylene, 1-butene, 1-pentene, 4-methyl-1-pentene, 1-hexene, 1-octene, 4,6-dimethyl-1-heptene, 1-decene, 1-dodecene.

A further object of the present invention is a catalyst system comprising the product obtainable by contacting:

a) a metallocene compound of formula (I);

b) at least an alumoxane or a compound able to form an alkylmetallocene cation; and c) optionally an organo aluminum compound.

Preferably the metallocene compound has formula (Va), (Vb), (Vc) or (Vd).

The following examples are given to illustrate and not to limit the invention.

EXAMPLES

The intrinsic viscosity (I.V.) was measured in tetrahydronaphtalene (THN) at 135° C.

The melting points of the polymers ($T_m$) were measured by Differential Scanning Calorimetry (D.S.C.) on a Perkin Elmer DSC-7 instrument, according to the standard method. A weighted sample (5-7 mg) obtained from the polymerization was sealed into aluminum pans and heated to 180° C. at 10° C./minute. The sample was kept at 180° C. for 5 minutes to allow a complete melting of all the crystallites, then cooled to 20° C. at 10° C./minute. After standing 2 minutes at 20° C., the sample was heated for the second time to 180° C. at 10° C./min. In this second heating run, the peak temperature was taken as the melting temperature ($T_m$) and the area of the peak as melting enthalpy ($\Delta H_f$).

Molecular weight parameters and molecular weight distribution for all the samples were measured using a Waters 150C ALC/GPC instrument (Waters, Milford, Mass., USA) equipped with four mixed-gel columns PLgel 20 μm Mixed-A LS (Polymer Laboratories, Church Stretton, United Kingdom). The dimensions of the columns were 300×7.8 mm. The solvent used was TCB and the flow rate was kept at 1.0 mL/min. Solution concentrations were 0.1 g/dL in 1,2,4 trichlorobenzene (TCB). 0.1 g/L of 2,6-di-t-butyl-4-methyl phenol (BHT) was added to prevent degradation and the injection volume was 300 μL. All the measurements were carried out at 135° C. GPC calibration is complex, as no well-characterized narrow molecular weight distribution standard reference materials are available for 1-butene polymers. Thus, a universal calibration curve was obtained using 12 polystyrene standard samples with molecular weights ranging from 580 to 13,200,000. It was assumed that the K values of the Mark-Houwink relationship were: $K_{PS}=1.21\times10^{-4}$, dL/g and $K_{PB}=1.78\times10^{-4}$ dL/g for polystyrene and poly-1-butene respectively. The Mark-Houwink exponents α were assumed to be 0.706 for polystyrene and 0.725 for poly-1-butene. Even though, in this approach, the molecular parameters obtained were only an estimate of the hydrodynamic volume of each chain, they allowed a relative comparison to be made.

NMR analysis. $^{13}$C-NMR spectra were acquired on a DPX-400 spectrometer operating at 100.61 MHz in the Fourier transform mode at 120° C. The samples were dissolved in 1,1,2,2-tetrachloroethane-d2 at 120° C. with a 8% wt/v concentration. Each spectrum was acquired with a 90° pulse, 15 seconds of delay between pulses and CPD (waltz16) to remove $^1H$-$^{13}C$ coupling. About 3000 transients were stored in 32 K data points using a spectral window of 6000 Hz. The isotacticity of metallocene-made PB is measured by $^{13}$C NMR, and is defined as the relative intensity of the mmmm pentad peak of the diagnostic methylene of the ethyl branch. This peak at 27.73 ppm was used as internal reference. Pentad assignments are given according to *Macromolecules,* 1992, 25, 6814-6817.

The side chain methylene region of PB spectrum was fitted using the routine for deconvolution included in the Bruker WIN-NMR program. The mmmm pentad and the pentads related to the single unit error (mmmr, mmrr and mrrm) were fitted using Lorenzian lineshapes, allowing the program to change the intensity and the width of the lines. As a result the relative intensities of those signals were obtained. These results were used for the statistical modelling of pentad distributions using an enantiomorphic site model, in order to obtain the complete pentad distribution, from which the triad distribution is derived.

Metallocene Compounds

Synthesis of Dimethylsilanediyl{5-(1,1,3,3,6-pentamethyl-1,2,3,5-tetrahydro-s-indacenyl)-7-(2,5-dimethyl-cyclopenta[1,2-b:4,3-b']-dithiophene)} Zirconium Dichloride [A-1]

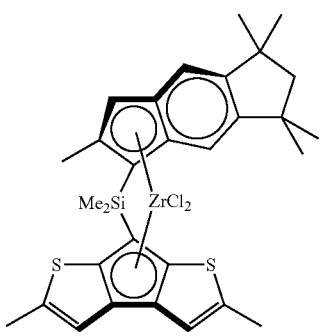

a) Synthesis of 1,1,3,3-tetramethylindane

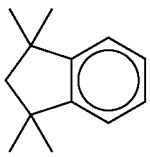

A mixture of 117.26 g of α-methylstyrene (Aldrich 99%, 0.98 mol) and 73.0 g of t-butanol (Aldrich 99%, 0.98 mol) was slowly added (in about 1 h) to a mixture of 200 g of acetic acid and 200 g of sulfuric acid, previously warmed at 40° C. The resulting suspension was stirred for 30 min at 40° C. and then the two layers obtained were separated. The aqueous layer was eliminated, while the organic layer was washed first with a 0.7 M NaOH aqueous solution until pH 7 (3×50 mL) and then with water (2×50 mL). The opaque yellow solution obtained was distilled under heating in vacuo. The colourless transparent liquid collected in the range of 97-103° C. at 11-26 mbar of pressure resulted to be by NMR analysis the desired pure 1,1,3,3 tetramethylindane (28.43 g, 16.6% isolated yield).

$^1$H-NMR (CDCl$_3$, δ, ppm): 1.39 (s, CH$_3$, H8 and H9, 12H); 1.99 (s, CH$_2$, H2, 2H); 7.17-7.30 (m, Ar, H4, H5, H6 and H7, 4H).

$^{13}$C{$^1$H}-NMR (CDCl$_3$, δ, ppm): 31.56 (CH$_3$, C8 and C9, 4C); 42.51 (C, C1 and C3, 2C); 56.60 (CH$_2$, C2, 1C); 122.45 and 126.69 (Ar, C4, C5, C6 and C7, 4C); 151.15 (Ar, C3a and C7a, 2C).

b) Synthesis of 2,5,5,7,7-pentamethyl-2,3,5,6,7-pentahydro-s-indacen-1-one

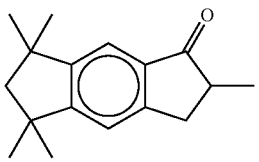

50.71 g of AlCl$_3$ (Aldrich 99%, 376.5 mmol) were slowly added at 0° C. (in 30 min) to a mixture of 28.43 g of 1,1,3,3 tetramethylindane (163.1 mmol) and 38.32 g of 2-bromoisobutyryl bromide (Aldrich 98%, 163.3 mmmol) in 500 mL of CH$_2$Cl$_2$. During the addition the solution turned from colourless to yellow and finally to dark red. Gas evolution was observed too. The suspension was stirred for 17 h at room temperature and then poured into 200 g of ice/water. The green organic layer was washed first with a 1 M HCl aqueous solution (1×200 mL), then with a saturated NaHCO$_3$ solution (2×200 mL) and finally with water (2×200 mL). The organic layer was dried over Na$_2$SO$_4$, filtered and evaporated to dryness under reduced pressure to give 38.23 g of a green solid, which resulted to contain 76.7% of the desired product by GC-MS (crude yield 96.7%). This solid was treated with 50 mL of MeOH and filtered. The white residue was washed once more with 30 mL of MeOH and dried giving 20.28 g of a white powder. The filtrate was stored at −20° C. for 24 h yielding 3.95 g of a white powder, which was collected with the previous one. The powder was characterized as pure 2,5,5,7,7-pentamethyl-2,3,5,6,7-pentahydro-s-indacen-1-one by NMR analysis. Isolated yield 61.3% (24.23 g).

$^1$H-NMR (CDCl$_3$, δ, ppm): 1.27 (s, CH$_3$, H9, 3H); 1.31 (s, CH$_3$, H11, 6H); 1.33 (s, CH$_3$, H10, 6H); 1.95 (s, CH$_2$, H6, 2H); 2.62-2.79 (m, CH$_2$ and CH, H2 and H3, 2H); 3.28-3.37 (m, CH$_2$, H3, 1H); 7.15 (s, Ar, H4, 1H); 7.51 (s, Ar, H8, 1H).

$^{13}$C{$^1$H}-NMR (CDCl$_3$, δ, ppm): 16.34 (CH$_3$, C9, 1C); 31.28, 31.30 (CH$_3$, C10, 2C); 31.50, 31.55 (CH$_3$, C11, 2C); 34.73 (CH$_2$, C3, 1C); 41.86 (C, C7, 1C); 42.38 (CH, C2, 1C); 42.52 (C, C5, 1C); 56.44 (CH$_2$, C6, 1C); 117.87 (Ar, C8, 1C); 120.22 (Ar, C4, 1C); 135.67 (Ar, C8a, 1C); 151.69 (Ar, C7a, 1C); 152.91 (Ar, C3a, 1C); 159.99 (Ar, C4a, 1C); 208.96 (C=O, C1, 1C).

c) 1,1,3,3,6-pentamethyl-1,2,3,5-tetrahydro-s-indacene

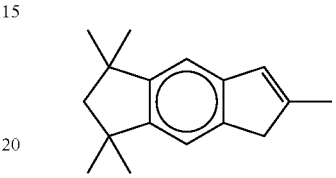

A suspension of 24.36 g of pure 2,5,5,7,7-pentamethyl-2,3,5,6,7-pentahydro-s-indacen-1-one (100.5 mmol) in 100 mL of ethanol was treated at room temperature with 4.06 g of NaBH$_4$ (Aldrich 98%, 105.2 mmol). An opaque yellowish solution was obtained. After 4.5 h stirring at room temperature, the solution was treated with 5 mL of acetone and then evaporated to dryness under reduced pressure to give a yellowish gel. The latter was treated with 100 mL of toluene and 40 mL of water and after 15 min stirring the two layers were separated. The aqueous layer was washed with 50 mL of toluene, while the organic layer was washed with a 10% NH$_4$Cl aqueous solution (2×30 mL). The organic layers were collected, dried over Na$_2$SO$_4$ and filtered. The yellow filtrate containing the desired alcohol was added of 1.89 g of p-toluenesulfonic acid monohydrate (Aldrich 98.5%, 9.8 mmol) and heated at 80° C. Formation of water and separation of two layers were observed. After 5 h stirring at 80° C. and 2 days at room temperature, the reaction mixture contained still 11% of starting alcohol by NMR analysis. Then the water formed was removed from the reaction mixture and 0.20 g of p-toluenesulfonic acid monohydrate (1.0 mmol) were added. After 1 h stirring at 80° C. and 16 h at room temperature, the conversion was quantitative. The final mixture was treated with 50 mL of a saturated NaHCO$_3$ aqueous solution. The organic layer was separated, washed once more with a saturated NaHCO$_3$ aqueous solution (1×50 mL) and water (3×50 mL), dried over Na$_2$SO$_4$ and filtered. The yellow filtrate was evaporated to dryness under reduced pressure to give 20.89 g of a yellow liquid, which crystallized after few minutes by standing at room temperature. This liquid was characterized as pure 1,1,3,3,6-pentamethyl-1,2,3,5-tetrahydro-s-indacene by NMR analysis. Isolated yield 91.8%.

$^1$H-NMR (CDCl$_3$, δ, ppm): 1.38 (s, CH$_3$, H9 e H10, 12H); 2.00 (s, CH$_2$, H2, 2H); 2.18 (bs, CH$_3$, H11, 3H); 3.30 (s, CH$_2$, H5, 2H); 6.51 (s, CH, H7, 1H); 7.06 (s, Ar, H8, 1H); 7.18 (s, Ar, H4, 1H).

$^{13}$C{$^1$H}-NMR (CDCl$_3$, δ, ppm): 16.81 (CH$_3$, C11, 1C); 31.77 (CH$_3$, C9 e C10, 4C); 42.08, 42.16 (C, C1 e C3, 2C); 42.28 (CH$_2$, C5, 1C); 57.04 (CH$_2$, C2, 1C); 113.61 (Ar, C8, 1C); 117.55 (Ar, C4, 1C); 127.13 (CH, C7, 1C); 142.28 (Ar, C4a, 1C); 145.00, 145.26 (Ar and C=, C7a and C6, 2C); 146.88 (Ar, C3a, 1C); 149.47 (Ar, C8a, 1C).

d) Synthesis of Chloro(1,1,3,3,6-pentamethyl-1,2,3,5-tetrahydro-s-indacen-5-yl)dimethylsilane

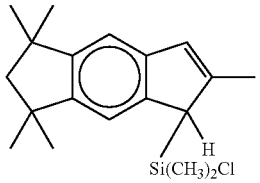

A 2.5 M n-BuLi solution in hexane (3.8 mL, 9.50 mmol, n-BuLi:indacene=1:1) was added dropwise at 0° C. to a solution of 2.16 g of 1,1,3,3,6-pentamethyl-1,2,3,5-tetrahydro-s-indacene (9.54 mmol) in 40 mL of $Et_2O$. At the end of the addition, the resulting light yellow solution was allowed to warm up to room temperature and stirred for 1 h with final formation of a white suspension. An aliquot of this suspension was quenched with $CD_3OD$ and dried: the related $^1H$ NMR analysis in $CDCl_3$ showed complete conversion of the starting indacene to the corresponding lithium salt. The latter was then cooled again to 0° C. and added to a solution of $Me_2SiCl_2$ (98%, 1.27 g, d=1.064, 9.64 mmol) in 10 mL of $Et_2O$, previously cooled to 0° C. too. The reaction mixture was allowed to warm up to room temperature and stirred for 16 h with final formation of a white suspension. After 40 min stirring at r.t. the conversion was ca. 80% by $^1H$ NMR analysis. The solvents were removed in vacuo and the residue extracted with 70 mL of toluene to remove the LiCl. The filtrate was brought to dryness in vacuo at 40° C. to give a thick yellow oil as product (3.03 g), which tended to crystallize by standing at room temperature. Isolated yield=97.9% (purity 97.9% wt. by $^1H$ NMR analysis). Starting indacene was still present in 2.1% wt.

$^1$H-NMR ($CDCl_3$, δ, ppm): 0.11 (s, 3H, Si—$CH_3$); 0.41 (s, 3H, Si—$CH_3$); 1.29 (s, 3H, $CH_3$); 1.31 (s, 9H, $CH_3$); 1.93 (s, 2H, $CH_2$); 2.24 (m, 3H, $CH_3$); 3.49 (s, 1H, CH); 6.57 (m, 1H, Cp-H); 7.03 (s, 1H, Ar); 7.16 (s, 1H, Ar).

e) Synthesis of 5-(1,1,3,3,6-pentamethyl-1,2,3,5-tetrahydro-s-indacenyl)-7-(2,5-dimethyl-cyclopenta[1,2-b:4,3-']-dithiophene) Dimethylsilane A 2.5 M solution of n-BuLi in hexane (3.60 mL, 9.00 mmol) was added dropwise at 0° C. to a suspension of 1.82 g of 2,5-dimethyl-7H-cyclopenta[1,2-b:4,3-b']-dithiophene (8.82 mmol) in 30 mL of $Et_2O$. The resulting brown suspension was stirred at 0° C. for 1 h and then added at the same temperature to a solution of 2.88 g of chloro(1,1,3,3,6-pentamethyl-1,2,3,5-tetrahydro-s-indacen-5-yl)dimethylsilane (97.9%, 8.84 mmol) in 20 mL of $Et_2O$, previously cooled to 0° C. too. The reaction mixture was kept at 0° C. for 10 min, then allowed to warm up to room temperature and stirred overnight with final formation of a black suspension. Few mL of MeOH were added, the solvents were evaporated under reduced pressure and the crude residue was extracted with 70 mL of toluene. The extract was dried in vacuo to give 4.46 g of a pitch-dark solid, which was analysed by $^1$H-NMR spectroscopy and GC-MS analysis. The latter showed the presence of the desired ligand in amount of 71.1% together with 1.8% of 1,1,3,3,6-pentamethyl-1,2,3,5-tetrahydro-s-indacene and 3.2% of $MeTh_2Cp$. A by-product with MW of 340 was also present in 11.8%: it could be n-butyl(1,1,3,3,6-pentamethyl-1,2,3,5-tetrahydro-s-indacen-5-yl)dimethylsilane. Crude yield=73.6%. Attempts to purify the product by washing with pentane failed, then the ligand was used as such in the next step without further purification.

$^1$H NMR (δ, ppm, $CDCl_3$): −0.37 (s, 3H, Si—$CH_3$); −0.34 (s, 3H, Si—$CH_3$); 1.26 (s, 3H, $CH_3$); 1.28 (s, 3H, $CH_3$); 1.32 (s, 3H, $CH_3$); 1.33 (s, 3H, $CH_3$); 1.92 (s, 2H, $CH_2$); 2.21 (s, 3H, $CH_3$); 2.55 (d, 6H, J=2.15 Hz, $CH_3$); 3.73 (s, 1H, CH); 3.95 (s, 1H, CH); 6.59 (s, 1H, Cp-H); 6.85 (m, 2H, CH); 7.07 (s, 1H, Ar); 7.15 (s, 1H, Ar).

m/z (%):489 (14) [$M^++1$], 488 (34) [$M^+$], 284 (28), 283 (100), 264 (13), 263 (60), 235 (10), 227 (13).

f) Synthesis of Dimethylsilanediyl{5-(1,1,3,3,6-pentamethyl-1,2,3,5-tetrahydro-s-indacenyl)-7-(2,5-dimethyl-cyclopenta[1,2-b:4,3-b']-dithiophene)} Zirconium Dichloride [A-1]

A 2.5 M solution of n-BuLi in hexane (6.60 mL, 16.50 mmol) was added dropwise at 0° C. to a light brown solution of 4.07 g of 5-(1,1,3,3,6-pentamethyl-1,2,3,5-tetrahydro-s-indacenyl)-7-(2,5-dimethyl-cyclopenta[1,2-b:4,3-b']-dithiophene) dimethylsilane (8.33 mmol) in 30 mL of $Et_2O$. The resulting brown suspension was stirred for 1 h at room temperature, then cooled again to 0° C. to add a suspension of 1.95 g of $ZrCl_4$ (8.37 mmol) in 20 mL of toluene, previously cooled to the same temperature. At the end of the addition the reaction mixture was allowed to warm up to room temperature and stirred for 1.5 h. The solvents were removed in vacuo and the dark orange-brown residue (containing mainly the expected product by $^1$H NMR analysis in $CDCl_3$) was treated with 60 mL of a mixture isobutanol/toluene 1/5 (v/v). After 10 min stirring at room temperature, the suspension was filtered on a G3 frit. The filtrate was eliminated, because its $^1$H NMR spectrum showed decomposition of the product due probably to the use of isobutanol; any attempts to recover the complex by extraction with toluene failed. The residue was dried in vacuo to give 0.43 g of a light orange powder, which resulted to be by $^1$H-NMR analysis the desired complex (with LiCl isolated yield=8.0%).

$^1$H NMR (δ, ppm, $CDCl_3$): 1.31 (s, 6H, Si—$CH_3$); 1.20 (s, 3H, $CH_3$); 1.27 (s, 3H, $CH_3$); 1.33 (s, 3H, $CH_3$); 1.36 (s, 3H, $CH_3$); 1.83 (s, 2H, $CH_2$); 2.33 (s, 3H, $CH_3$); 2.36 (d, 3H, J=0.98 Hz, $CH_3$); 2.57 (d, 3H, J=0.98 Hz, $CH_3$); 6.60 (q, 1H, J=0.98 Hz, CH); 6.74 (s, 1H, Cp-H); 6.76 (q, 1H, J=0.98 Hz, CH); 7.18 (s, 1H, Ar); 7.29 (s, 1H, Ar).

Polymerization (General Procedure)

The cocatalyst methylalumoxane (MAO) was a commercial product which was used as received (Witco AG, 10% wt/vol toluene solution, or Albemarle, 30% wt/wt). The catalyst mixture was prepared by dissolving the amount of the metallocene indicated in table 1 with the proper amount of the MAO solution, (Al/Zr ratio=500) obtaining a solution which was stirred for 10 min at room temperature before being injected into the autoclave.

6 mmol of $Al(i-Bu)_3$ (as a 1M solution in hexane) and 1350 g of 1-butene were charged at room temperature in a 4-L jacketed stainless-steel autoclave, equipped with magnetically driven stirrer and a 35-mL stainless-steel vial, connected to a thermostat for temperature control, previously purified by washing with an $Al(i-Bu)_3$ solution in hexanes and dried at 50° C. in a stream of nitrogen. The autoclave was then thermostated at the polymerization temperature, and then the toluene solution containing the catalyst/cocatalyst mixture was injected in the autoclave by means of nitrogen pressure through the stainless-steel vial, and the polymerization carried out at constant temperature for the time indicated in Table 1. Then stirring is interrupted; the pressure into the autoclave is raised to 20 bar-g with nitrogen. The bottom discharge valve is opened and the 1-butene/poly- 1-butene mixture is discharged into a heated steel tank containing water at 70° C. The tank heating is switched off and a flow of nitrogen at 0.5 bar-g is fed. After cooling at room temperature, the steel tank is opened and the wet polymer collected. The wet polymer is dried in an oven under reduced pressure at 70° C. The polymerization conditions and the characterization data of the obtained polymers are reported in Table 1.

TABLE 1

| Ex | Comp. | mg | Yield (g) | Activity kg/ ($g_{cat}$·h) | I.V. dL/g | $T_m$(II) °C. | $\Delta H_f$(II) J/g | mmmm % |
|---|---|---|---|---|---|---|---|---|
| 1 | A-1 | 2 | 32 | 16.0 | 1.31 | 71.3 | 12.9 | 77.9 |
| 2 | A-1 | 4 | 151 | 37.8 | 0.91 | 70.5 | 7.4 | 76.5 |

The physical-mechanic characteristics of the 1-butene homopolymer obtained in example 2 was analyzed according to ISO 527-1 and ISO 178. The results are reported in table 2

TABLE 2

| Measurement | Units | |
|---|---|---|
| flexural modulus (ISO 178) | MPa | 128.0 |
| Stress at yield | MPa | 6.5 |
| Elongation at yield | % | 15.0 |
| Stress at break | MPa | 26.8 |
| Elongation at break | % | 485 |

Preparation of 1-Butene Homopolymer Component B)

Rac dimethylsilandiylbis-6-[2,5-dimethyl-3-(2'-methyl-phenyl)cyclopentadienyl-[1,2-b]-thiophene]zirconium dichloride (A-2), was prepared according to WO01/44318.

The cocatalyst methylalumoxane (MAO) was a commercial product which was used as received (Witco AG, 10% wt/vol toluene solution, 1.7 M in Al).

The catalyst mixture was prepared by dissolving 2 mg of A-2 in 8 ml of toluene with the proper amount of the MAO solution (Al/Zr=500), obtaining a solution which was stirred for 10 min at room temperature before being injected into the autoclave.

4 mmol of Al(i-Bu)$_3$ (TIBA) (as a 1 M solution in hexane) and 712 g of 1-butene were charged, at room temperature, in a 2.3-L jacketed stainless-steel autoclave, equipped with magnetically driven stirrer and a 35-mL stainless-steel vial, connected to a thermostat for temperature control. The autoclave was then thermostatted at 83° C. and the catalyst system, prepared as reported above, was injected in the autoclave by means of nitrogen pressure through the stainless-steel vial. The temperature was rapidly raised to 85° C. and the polymerization was carried out at constant temperature, for 1 hour.

After cooling the reactor to room temperature, the polymer was dried under reduced pressure, at 60° C. The polymer obtained has an Intrinsic viscosity (I.V. THN at 135° C.) of 0.9 a molecular weight distribution (Mw/Mn) of 2.2, a melting point of 106° C. and isotactic pentads (mmmm) higher than 98%.

Preparation of 1-Butene Polymer Composition

The 1-butene polymer obtained in example 2 (component A) was co-extruded with the 1-butene polymer (component B) obtained as described above by using a Brandbury extruder in a 1:1 weight ratio. 0.1% by weight of Inoganox™ 1010 as stabilizer was added in the composition. The characteristics of the composition compared with the characteristics of the 1-butene homopolymers (components A and B) are reported on table 3.

TABLE 3

| | $T_m$(II) °C. | mmmm % | flexural modulus (ISO 178) |
|---|---|---|---|
| component a | 71 | 76.5 | 128 |
| component b | 106 | >98 | 405 |
| 50:50 comp a:comp b | 99 | n.a. | 277 | n.a. not available

From table 3 it results that the 1-butene polymer composition has a synergetic effect to retain the feature of the low modulus due to component a) and at the same time to have a quite high melting point due to component b).

The invention claimed is:

1. A process for preparing 1-butene polymers optionally comprising up to 30% by mol of units derived from at least one monomer selected from ethylene, propylene or an alpha-olefin of formula $CH_2$=CHZ', wherein Z' is a $C_3$-$C_{10}$ alkyl group, comprising polymerizing 1-butene and optionally ethylene, propylene or said alpha-olefin, in presence of a catalyst system obtained by contacting:

a) a metallocene compound of formula (I):

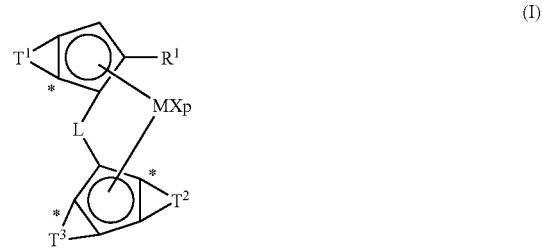

wherein

M is a transition metal belonging to group 3, 4, 5, or 6, or to a lanthanide or actinide group in the Periodic Table of Elements;

p is an integer from 0 to 3, and is equal to a formal oxidation state of M minus 2;

X, same or different, is hydrogen, a halogen, R, OR, $OSO_2CF_3$, OCOR, SR, $NR_2$, or $PR_2$, wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally comprising at least one heteroatom belonging to groups 13-17 of the Periodic Table of Elements; or two X optionally form a substituted or unsubstituted butadienyl radical, or OR'O, wherein R' is a divalent radical selected from a $C_1$-$C_{40}$ alkylidene, a $C_6$-$C_{40}$ arylidene, a $C_7$-$C_{40}$ alkylarylidene and a $C_7$-$C_{40}$ arylalkylidene radical;

L is a divalent $C_1$-$C_{40}$ hydrocarbon radical optionally comprising at least one heteroatom belonging to groups 13-17 of the Periodic Table of Elements, or a divalent silvlidene radical comprising at least one, and up to 5 silicon atoms;

$R^1$ is a $C_1$-$C_{40}$ hydrocarbon radical optionally comprising at least one heteroatom belonging to groups 13-17 of the Periodic Table of Elements;

$T^1$ is a moiety of formula (IIa) or (IIb):

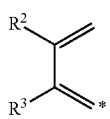

(IIa)

wherein the atom marked with the symbol * bonds to the atom marked with the same symbol in the compound of formula (I);

$R^2$ and $R^3$ same or different, are $C_1$-$C_{40}$ hydrocarbon radicals optionally comprising at least one heteroatom belonging to groups 13-17 of the Periodic Table of Elements, or together form a condensed, saturated or unsaturated $C_3$-$C_7$-membered ring optionally comprising at least one heteroatom belonging to groups 13-16 of the Periodic Table of Elements, wherein every atom forming said condensed, saturated or unsaturated $C_3$-$C_7$-membered ring is substituted with an $R^8$ radical;

$R^8$, same or different, is hydrogen or a $C_1$-$C_{40}$ hydrocarbon radical;

$R^4$ is a $C_1$-$C_{40}$ hydrocarbon radical optionally comprising at least one heteroatom belonging to groups 13-17 of the Periodic Table of Elements;

$T^2$ and $T^3$, same or different, are a moiety of formula (IIIa) or (IIIb):

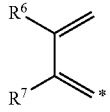

(IIIa)

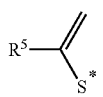

(IIIb)

wherein the atom marked with the symbol * bonds to the atom marked with the same symbol in the compound of formula (I);

$R^6$ and $R^7$, same or different, are hydrogen or $C_1$-$C_{40}$ hydrocarbon radicals optionally comprising at least one heteroatom belonging to groups 13-17 of the Periodic Table of Elements; and $R^5$ is hydrogen or a $C_1$-$C_{40}$ hydrocarbon radical optionally comprising at least one heteroatom belonging to groups 13-17 of the Periodic Table of Elements;

with the provisos that if $T^1$ is a moiety of formula (IIa), at least one of $T^2$ or $T^3$ is a moiety of formula (IIIb); and b) at least one alumoxane or a compound capable of forming an alkylmetallocene cation, wherein the 1-butene polymers comprise isotactic pentads (mmmm) between 40% and 80%.

2. A process for preparing 1-butene polymers optionally comprising up to 30% by mol of units derived from at least one monomer selected from ethylene, propylene or an alpha-olefin of formula $CH_2=CHZ'$, wherein Z' is a $C_3$-$C_{10}$ alkyl group, comprising polymerizing 1-butene and optionally ethylene, propylene or said alpha-olefin, in presence of a catalyst system obtained by contacting:

a) a metallocene compound of formula (I):

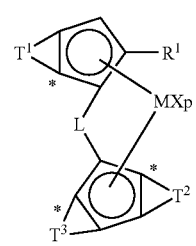

(I)

wherein

M is a transition metal belonging to group 3, 4, 5, or 6, or to a lanthanide or actinide group in the Periodic Table of Elements;

p is an integer from 0 to 3, and is equal to a formal oxidation state of M minus 2;

X, same or different, is hydrogen, a halogen, R, OR, $OSO_2CF_3$, OCOR, SR, $NR_2$, or $PR_2$, wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally comprising at least one heteroatom belonging to groups 13-17 of the Periodic Table of Elements; or two X optionally form a substituted or unsubstituted butadienyl radical, or OR'O, wherein R' is a divalent radical selected from a $C_1$-$C_{40}$ alkylidene, a $C_6$-$C_{40}$ arylidene, a $C_7$-$C_{40}$ alkylarylidene and a $C_7$-$C_{40}$ arylalkylidene radical;

L is a divalent $C_1$-$C_{40}$ hydrocarbon radical optionally comprising at least one heteroatom belonging to groups 13-17 of the Periodic Table of Elements, or a divalent silylidene radical comprising at least one, and up to 5 silicon atoms;

$R^1$ is a $C_1$-$C_{40}$ hydrocarbon radical optionally comprising at least one heteroatom belonging to groups 13-17 of the Periodic Table of Elements;

$T^1$ is a moiety of formula (IIa) or (IIb):

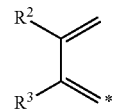

(IIa)

wherein the atom marked with the symbol * bonds to the atom marked with the same symbol in the compound of formula (I);

$R^2$ and $R^3$, same or different, are $C_1$-$C_{40}$ hydrocarbon radicals optionally comprising at least one heteroatom belonging to groups 13-17 of the Periodic Table of Elements, or together form a condensed, saturated or unsaturated $C_3$-$C_7$-membered ring optionally comprising at least one heteroatom belonging to groups 13-16 of the Periodic Table of Elements, wherein every atom forming said condensed, saturated or unsaturated $C_3$-$C_7$-membered ring is substituted with an $R^8$ radical;

$R^8$, same or different, is hydrogen or a $C_1$-$C_{40}$ hydrocarbon radical;

$R^4$ is a $C_1$-$C_{40}$ hydrocarbon radical optionally comprising at least one heteroatom belonging to groups 13-17 of the Periodic Table of Elements;

T² and T³, same or different, are a moiety of formula (IIIa) or (IIIb):

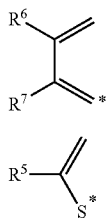

(IIIa)

(IIIb)

wherein the atom marked with the symbol * bonds to the atom marked with the same symbol in the compound of formula (I);

R⁶ and R⁷, same or different, are hydrogen or $C_1$-$C_{40}$ hydrocarbon radicals optionally comprising at least one heteroatom belonging to groups 13-17 of the Periodic Table of Elements; and R⁵ is hydrogen or a $C_1$-$C_{40}$ hydrocarbon radical optionally comprising at least one heteroatom belonging to groups 13-17 of the Periodic Table of Elements;

with the provisos that if T¹ is a moiety of formula (IIa), at least one of T² or T³ is a moiety of formula (IIIb); and b) at least one alumoxane or a compound capable of forming an alkylmetallocene cation, wherein the 1-butene polymers comprise isotactic pentads (mmmm) between 50% and 75%.

3. The process of claim 1, wherein the 1-butene polymers comprise a flexural modulus (FM) (ISO 527-1) between 50 and 200 MPa.

4. The process of claim 1, wherein the 1-butene polymers comprise a flexural modulus (FM) (ISO 527-1) between 50 and 150 MPa.

5. The process of claim 1, wherein the 1-butene polymers comprise a melting point (Tm) between 40° C. and 80° C.

6. The process of claim 1, wherein the 1-butene polymers comprise a melting point (Tm) between 45° C. and 75° C.

7. The process of claim 1, wherein the 1-butene polymers comprise a melting point (Tm) between 50° C. and 72° C.

8. The process of claim 1, wherein the 1-butene polymers comprise an intrinsic viscosity (I.V.) higher than 0.5 dl/g, measured in tetrahydronaphthalene (THN) at 135° C.

9. The process of claim 1, wherein the 1-butene polymers comprise an intrinsic viscosity (I.V.) equal to or higher than 0.8 dl/g, measured in tetrahydronaphthalene (THN) at 135° C.

10. The process of claim 1, wherein the 1-butene polymers comprise an intrinsic viscosity (I.V.) higher than 1 dl/g, measured in tetrahydronaphthalene (THN) at 135° C.

11. The process of claim 1, wherein the 1-butene polymers comprise an intrinsic viscosity (I.V.) higher than 1.2 dl/g, measured in tetrahydronaphthalene (THN) at 135° C.

12. The process of claim 1, wherein the 1-butene polymers comprise a molecular weight distribution (Mw/Mn) less than 4.

13. The process of claim 1, wherein the 1-butene polymers comprise a molecular weight distribution (Mw/Mn) less than 3.5.

14. The process of claim 1, wherein the 1-butene polymers comprise a molecular weight distribution (Mw/Mn) less than 3.

15. A 1-butene polymer composition comprising:
A) from 1 to 90% by weight of a 1-butene homopolymer, the 1-butene homopolymer comprising
a flexural modulus (FM) (ISO 527-1) between 50 and 200 MPa;
a melting point (Tm) between 40° C. and 80° C.;
an intrinsic viscosity (I.V.), measured in tetrahydronaphtalene (THN) at 135° C., higher than 0.5 dl/g; and
isotactic pentads (mmmm) between 40% and 80%;
wherein the flexural modulus (FM) (Mpa) and the melting point (Tm) (° C.) meet the following relation:

$$FM < 0.006 Tm^{2.44}; \text{ and}$$

B) from 10 to 90% by weight of a 1-butene homopolymer, or a 1-butene copolymer comprising up to 30% by mol of derived units of ethylene; propylene or at least one alpha-olefin of formula $CH_2=CHZ'$, wherein Z' is a $C_3$-$C_{10}$ alkyl group, the 1-butene homopolymer or 1-butene copolymer comprising
a melting point (Tm) higher than 90° C.; and
an isotactic pentads content (mmmm) higher than 90%.

16. The 1-butene polymer composition according to claim 15, wherein both A) and B) are 1-butene homopolymers.

* * * * *